(12) United States Patent
Clark

(10) Patent No.: US 6,398,735 B1
(45) Date of Patent: Jun. 4, 2002

(54) DETECTING A RELATIVE LEVEL OF AN ULTRASOUND IMAGING CONTRAST AGENT

(75) Inventor: David W Clark, Windham, NH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/519,700

(22) Filed: Mar. 7, 2000

(51) Int. Cl.[7] ................................ A61B 8/14
(52) U.S. Cl. ................................ 600/458
(58) Field of Search .................. 600/437, 440, 600/443, 447, 453, 458, 454, 420; 424/9.4, 9.6, 9.51, 9.52

(56) References Cited

U.S. PATENT DOCUMENTS

| 5,456,257 A | 10/1995 | Johnson et al. | |
|---|---|---|---|
| 5,577,505 A | 11/1996 | Brock-Fisher et al. | |
| 5,800,357 A | 9/1998 | Witt et al. | |
| 5,833,613 A | 11/1998 | Averkiou et al. | |
| 5,860,931 A * | 1/1999 | Chandler | 600/458 |
| 5,879,303 A | 3/1999 | Averkiou et al. | |
| 5,961,464 A * | 10/1999 | Poland | 600/458 |
| 6,080,107 A * | 6/2000 | Poland | 600/458 |
| 6,146,330 A * | 11/2000 | Tujino et al. | 600/443 |
| 6,149,597 A * | 11/2000 | Kamiyama | 600/458 |
| 6,258,033 B1 * | 7/2001 | Grenon | 600/458 |

* cited by examiner

Primary Examiner—Marvin M. Lateef
Assistant Examiner—Ali M. Imam (57) ABSTRACT

A method for detecting a relative level of a contrast agent in a region of a body, where the contrast agent is susceptible to destruction by a destructive ultrasound signal. The method comprises the steps of: determining a signal level from a first ultrasound echo that is produced in the region during a first time, which occurs while the contrast agent is present in the region; determining a signal level of a second ultrasound echo that is produced in the region during a second time, which occurs after destruction of the contrast agent; and determining a ratio of the signal level from the first ultrasound echo and the signal level from the second ultrasound echo, where the ratio indicates a relative level of the contrast agent during the second time as compared to the first time.

37 Claims, 3 Drawing Sheets

DETECTING A RELATIVE LEVEL OF AN ULTRASOUND IMAGING CONTRAST AGENT

FIELD OF THE INVENTION

The present invention relates to ultrasound imaging and, more particularly, to detection of a level of a contrast agent, where the contrast agent is susceptible to destruction by an ultrasound signal.

BACKGROUND OF THE INVENTION

Ultrasonic diagnostic imaging systems are capable of imaging and measuring the physiology within the body in a completely noninvasive manner. Ultrasonic waves are transmitted into the body from the surface of the skin and are reflected from tissue and cells within the body. The reflected echoes are received by an ultrasonic transducer and processed to produce an image or measurement of blood flow. Diagnosis is thereby possible with no intervention into the body of the patient.

Materials known as ultrasonic contrast agents can be introduced into the body to enhance ultrasonic diagnosis. Contrast agents are substances that strongly interact with ultrasonic waves, and return echoes that may be clearly distinguished from those returned by blood and tissue. One class of substance that has been found to be especially useful as an ultrasonic contrast agent is encapsulated gas, in the form of microbubbles.

Microbubbles present a significant acoustic impedance mismatch in the body, and a nonlinear behavior in certain acoustic fields that is readily detectable through special ultrasonic processing. Gases that have been stabilized in solutions in the form of tiny microbubbles are infused into the body and survive passage through the pulmonary system and circulate throughout the vascular system. Microbubble contrast agents are useful for imaging the body's vascular system, for instance, as the contrast agent can be injected into the bloodstream and will pass through the veins and arteries of the body with the blood supply until filtered from the blood stream in the lungs, kidneys and liver.

A coated microbubble is a microbubble contrast agent that is covered with a thin biodegradable coating or shell. Coated microbubbles are suspended in an aqueous solution for infusion into the blood stream. Coated microbubbles have the advantage of being stable in the body for a significant period of time, as the shells serve to protect the gases of the microbubbles from diffusion into the bloodstream. A size for the microbubbles is chosen to enable the microbubbles to pass through capillary beds.

At moderately high sound pressure amplitudes the acoustic pressure waves can cause the shells of coated microbubbles to rupture, freeing the bubbles to behave as non-coated microbubbles until they diffuse into the bloodstream. Acoustic energy can induce a microbubble to move in a nonlinear manner, itself a detectable ultrasonic phenomenon.

In some applications, a user of an ultrasound system may wish to distinguish a region into which blood flows rapidly from a region into which blood perfuses. Blood flow, as compared to perfusion, is a relatively fast, higher rate of blood transfer, such as that found in a heart ventricle, an artery or a vein. On the other hand, perfusion is a relatively slow diffusion of blood through a network of capillaries in an organ, such as the myocardium.

Ultrasound imaging and measurement of blood flow is relatively easy as compared to imaging and measurement of perfusion. Ultrasound echoes from higher flow rates can be separated from tissue echoes, which have greater magnitudes, by evaluating signal components that change phase quickly between successive measurements at a given location. For example, flowing blood can be distinguished from stationary tissue on a basis of a Doppler frequency shift of an echo signal.

The Doppler technique is not effective for perfusion imaging because an organ through which the blood is perfusing often moves substantially as compared to the relatively slow movement of the perfusing blood. Consequently, the blood cannot be distinguished from the organ. This situation is particularly relevant in a case where the heart muscle is being imaged.

Presently, the most sensitive method for imaging myocardial perfusion is through the use of coated microbubble contrast agents. There is a significant difference between the magnitude of an echo produced by a microbubble during destruction, as compared to an echo produced after the gas has dissipated. Accordingly, a region into which blood is perfusing can be recognized by evaluating two imaging frames in rapid succession, where a contrast agent is destroyed in the first frame, and then found to be absent from the region during the second frame.

U.S. Pat. No. 5,456,257, to Johnson et al., entitled "Ultrasonic Detection Of Contrast Agents", (hereinafter "the Johnson et al. patent") describes a technique for detecting microbubbles through phase insensitive detection of microbubble destruction and differentiation of the detected signals on a spatial basis. A first ultrasonic pulse destroys the microbubbles in a tissue region and these destruction events are received and envelope detected. A second pulse is transmitted to the same locations, and the. returning echoes, ideally, show an absence of microbubbles at the locations where the microbubbles were destroyed. The second set of echoes is subtracted from the first set on a spatial basis, yielding difference signals of substantial magnitude at the locations where the microbubbles were destroyed.

The method of subtracting envelope-detected signals as described in the Johnson et al. patent suffers from poor sensitivity and susceptibility to clutter caused by echoes from structures other than an organ of interest. Unfavorably, this method also responds directly to a system gain change. Consequently, a user may not clearly determine whether an image represents blood perfusion, or lack thereof, or an artifact of the system gain.

Accordingly, there is a need for an improved method for detecting a relative level of a contrast agent in a region of a body.

There is also a need for such a method that further distinguishes between a flow of blood into the region and a perfusion of blood into the region.

Furthermore, there is a need for an ultrasound system that employs the'improved method for detecting a relative level of a contrast agent in a region of a body.

SUMMARY OF THE INVENTION

In accordance with a first embodiment of the invention, a method is provided for detecting a relative level of a contrast agent in a region of a body, where the contrast agent is susceptible to destruction by a destructive ultrasound signal. The method comprises the steps of: determining a signal level from a first ultrasound echo that is produced in the region during a first time, which occurs while the contrast agent is present in the region; determining a signal level of a second ultrasound echo that is produced in the region during a second time, which occurs after destruction of the contrast agent; and determining a ratio of the signal level from the first ultrasound echo and the signal level from the second ultrasound echo, where the ratio indicates a relative level of the contrast agent during the second time as compared to the first time.

In accordance with a second embodiment of the invention, a method is provided for detecting a relative level of a contrast agent in a region of a body, where the contrast agent is susceptible to destruction by a destructive ultrasound signal. The method comprises the steps of determining an average signal level from a plurality of ultrasound echoes that are produced in a plurality of spatial subsets of the region; determining a signal level from an ultrasound echo that is produced in at least one spatial subset of the region; and determining an arithmetic relationship between the average signal level and the signal level, where the arithmetic relationship indicates a relative level of the contrast agent in the at least one spatial subset as compared to the plurality of spatial subsets.

A system is also provided for performing each of the methods.

DETAILED DESCRIPTION OF THE PREFERRED EMBODIMENTS

FIGS. 1–4 are functional block diagrams of several embodiments of a system for detecting a relative level of a contrast agent in accordance with the present invention. Each of the several embodiments performs a method that includes steps corresponding to the functional blocks. Any of these several variations can be implemented in hardware using either discrete components or modular circuitry. The system can also be implemented in firmware, using programmable components, or implemented in software for execution by a general-purpose processor.

As discussed below, the systems use either a magnitude ratio or a power ratio of clutter-filtered signals to evaluate a relative level of a contrast agent. Such techniques reduce susceptibility to errors introduced by system gain variations or clutter. Favorably, these systems provide good sensitivity, clutter rejection and motion immunity.

Figure 3:
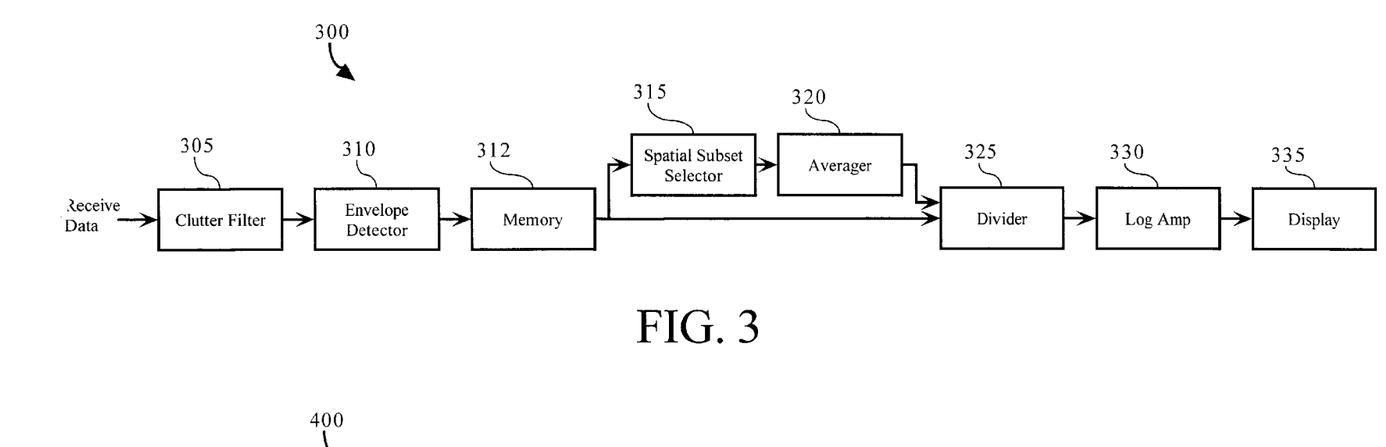
FIG. 3 is a functional block diagram of another embodiment of a system for detecting a relative level of a contrast agent in accordance with the present invention.
Figure 4:
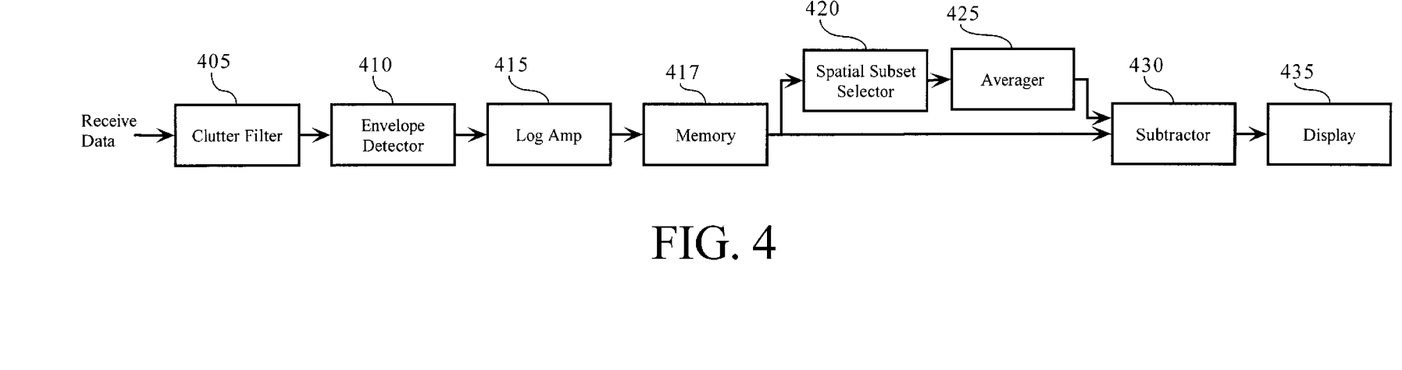
FIG. 4 is a functional block diagram of a variation of the system represented in FIG. 3.

Additionally, the embodiments shown in FIGS. 3 and 4 determine a ratio using an average signal level derived from ultrasound echoes taken from throughout a region of interest. Such a ratio has a tendency to reduce distortion of an image caused by a spatial coherence of a detected signal as compared to a spatial resolution of a displayed image. This distortion is conventionally known as speckle. The use of an average signal level in the ratio reduces speckle because the ratio has only one source of speckle rather than two sources.

If the reference averaging is performed in a polar space before scan conversion in an imaging system, then it can be weighted with a radial distance to reduce geometric distortion.

Figure 1:
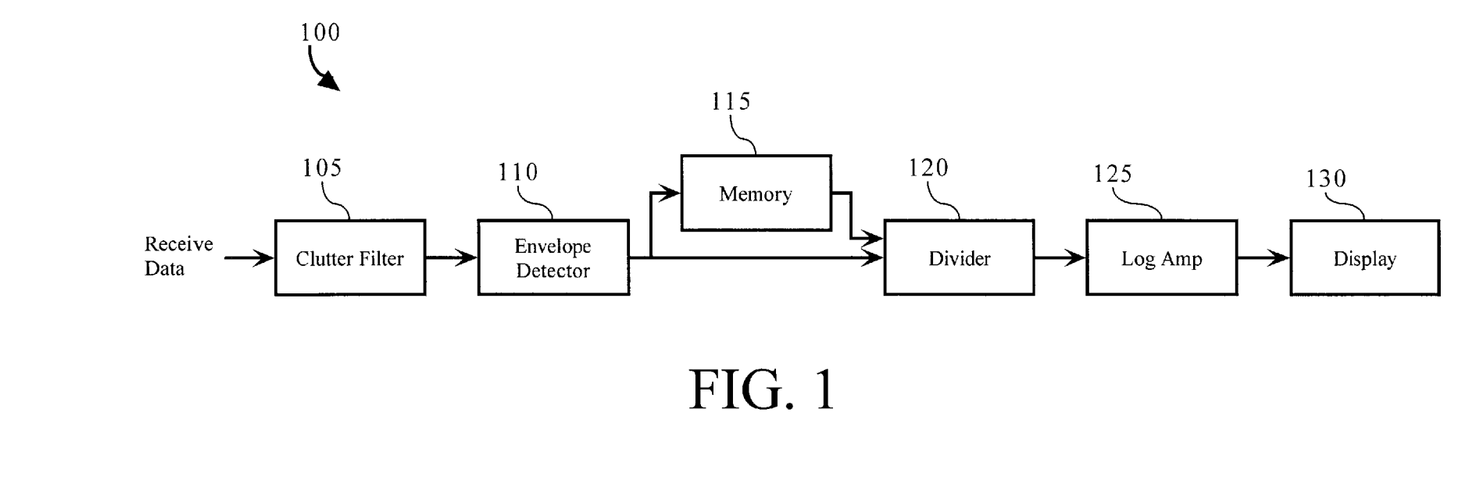
FIG. 1 is a functional block diagram of a system for detecting a relative level of a contrast agent in accordance with the present invention.

FIG. 1 is a block diagram of a system 100 which is a first embodiment of a system for detecting a relative level of a contrast agent. System 100 includes a clutter filter 105, an envelope detector 110, a memory 115, a divider 120, a log amplifier 125, and a display 130.

Clutter filter 105 receives data representing an ultrasound echo from a region of interest in a patient's body. It attenuates stationary or very slowly changing ultrasound echo data so that a weak echo that is moving or changing can be detected. An output of clutter filter 105 is routed to envelope detector 110.

Envelope detector 110 receives the output from clutter filter 105. It detects an instantaneous signal level of an ultrasound echo, regardless of an instantaneous phase angle of the echo. The signal level is directly related to the concentration of the contrast agent in the region of interest. The signal level is also related to other factors such as system gain, filter characteristics, and attenuation of the echo as it propagates through the body. However, taking a ratio of signals tends to minimize the effect of these other factors on the signal level. Because of the use of log amplifier 125, as discussed below, the instantaneous signal can be either a magnitude or a power of the ultrasound echo. Geometrically, the instantaneous signal can be represented as a phasor in a complex plane, i.e., having a real axis and an imaginary axis, where the detected envelope is a radius, or radius squared, of the phasor as a function of time. An output of envelope detector 110 is routed to memory 115 and also provided as an input to divider 120.

Memory 115 receives a signal level from envelope detector 110. It stores and subsequently provides the signal level to another input of divider 120.

Divider 120 receives two inputs, one from memory 115 and one from envelope detector 110, and divides one by the other to produce a ratio. More particularly, it receives a first signal level from memory 115 and a second signal level from envelope detector 110, and produces an output that is a ratio of the two signal levels. As explained below, the ratio indicates a relative level of the contrast agent present in the region of interest at a second time as compared to a first time. The ratio is provided as an input to log amplifier 125.

Log amplifier 125 receives the ratio from divider 120 and produces a logarithm of the ratio. This logarithmic operation effectively compresses the dynamic range of the ratio, making it more suitable for display. Because of the use of log amplifier 125, the instantaneous signal level detected by envelope detector 110 can be either a magnitude or a power level, since a logarithm of these parameters differs only by a constant scale factor of 2 in the log value. The output of log amplifier 125 is routed to display 130.

Display 130 receives the logarithm of the ratio and processes it to produce an image. As explained below, display 130 also determines whether blood is perfusing into a region of interest based on the relative level of the contrast agent. Other image processing options include (1) showing a relative degree of perfusion, such as with brightness or color, (2) determining an absolute degree of perfusion, such as by calibrating with a reference, and (3) determining a rate of re-perfusion, such as by varying the time interval between imaging frames.

In operation, the components of system 100 collectively execute a method for detecting a relative level of a contrast agent in a region of a body. The contrast agent is susceptible to destruction by a destructive ultrasound signal. The method includes the steps of (a) determining a signal level from a first ultrasound echo that is produced in the region during a first time, which occurs while the contrast agent is present in the region; (b) determining a signal level of a second ultrasound echo that is produced in the region during a second time, which occurs after destruction of the contrast agent; and (c) determining a ratio of the signal level from the first ultrasound echo and the signal level from the second ultrasound echo, where the ratio indicates a relative level of the contrast agent during the second time as compared to the first time.

The system produces a ratio by dividing a clutter-filtered magnitude or power signal level that is produced after destruction of the contrast agent, by a clutter-filtered magnitude or power signal level from an echo that is produced before or at a time of contrast agent destruction.

$$\text{Instantaneous Magnitude}_2 : \text{Instantaneous Magnitude}_1$$

or $$\text{Instantaneous Power}_2 : \text{Instantaneous Power}_1$$

These ratios are indicative of a relative level of the contrast agent during the second time as compared to the first time. However, a particular designation of a signal level as either a numerator or a denominator is not critical to the operation of the invention.

Envelope detector 110 determines a signal level from a first ultrasound echo that is produced in the region during a first time, which occurs while the contrast agent is present in the region. The signal level from the first ultrasound echo is stored in memory 115, which further provides the first signal level as a first input to divider 120.

Subsequently, envelope detector 110 determines a signal level of a second ultrasound echo that is produced in the region during a second time, which occurs after destruction of the contrast agent. The signal level from the second ultrasound echo is provided as a second input to divider 120.

Divider 120 determines a ratio of the signal level from the first ultrasound echo and the signal level from the second ultrasound echo. The ratio indicates a relative level of the contrast agent during the second time as compared to the first time. A ratio can be produced either by dividing the first signal by the second, or vice versa.

The ratio is routed to log amplifier 125, which provides a logarithm of the ratio of the signal level from the first ultrasound echo and the signal level from the second ultrasound echo to display 130 for further processing.

Recall that a flow of blood into a region occurs at a substantially greater rate than a perfusion of blood into the region. Accordingly, display 130 can detect a perfusion of blood into the region based on the relative level of the contrast agent during the second time as compared to the first time. Assume that the ratio is constructed with the signal level from the second ultrasound echo in the numerator and the signal from the first ultrasound echo in the denominator. If this ratio is approximately equal to 1, then the level of contrast agent present during the second time is approximately the same as the level present during the first time, indicating that the region can be one into which blood flows, or indicating that the region can be one into which blood neither flows nor perfuses. However, if this ratio is substantially less than 1, then the level of contrast agent during the second time is significantly less than the level during the first time, indicating that the region was not re-populated with the contrast agent, and further indicating that the region is likely to be one into which blood perfuses. One can increase the level of confidence regarding the detection of the perfusion of blood into the region by repeating the measurements of the signal levels for multiple pairs of imaging frames, and also by averaging the measurements over small spatial regions to reduce speckle variance.

System 100 detects movement or change of matter in a sub-region by performing multiple scans of the sub-region, and looking for a change in the images produced by the scans. A packet is a set of data from multiple scans of the same sub-region. A frame is an interval of time during which a packet is collected from each of the sub-regions in a region of interest. Preferably, the clutter-filtered signal levels are averaged over a packet, or a part of a packet, and the averages are separated by one frame time. That is, the signal level from the first ultrasound echo is an average signal level from a plurality of ultrasound echoes that are produced before, or at a time of, destruction of the contrast agent, and the signal level from the second ultrasound echo is an average signal level from a plurality of ultrasound echoes that are produced after destruction of the contrast agent. The steps of determining a signal level from a first ultrasound echo and determining a signal level of a second ultrasound echo are executed, respectively, in consecutive ultrasound imaging frames.

Figure 2:
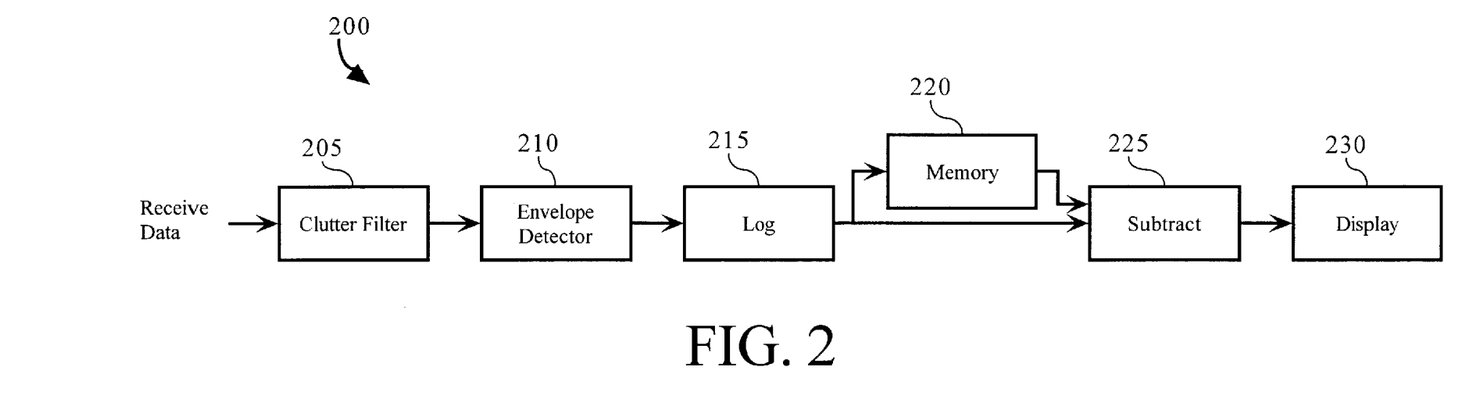
FIG. 2 is a functional block diagram of a variation of the system represented in FIG. 1.

FIG. 2 is a block diagram of a system 200, which is a variation of system 100 shown in FIG. 1. System 200 includes a clutter filter 205, an envelope detector 210, a log amplifier 215, a memory 220, a subtractor 225 and a display 230. Clutter filter 205, envelope detector 210 and display 230 function similarly to clutter filter 105, envelope detector 110 and display 130, respectively, as discussed above.

System 200 and system 100 differ in the manner in which they determine a logarithm of a ratio of two signals. Mathematically, a logarithm of a ratio is equal to the logarithm of the numerator minus the logarithm of the denominator. System 200 determines a difference between a logarithm of a signal level from a first ultrasound echo and a logarithm of a signal level from a second ultrasound echo. This difference yields a logarithm of a ratio of the signal level from the first ultrasound echo and the signal level from the second ultrasound echo.

Clutter filter 205 receives data representing an ultrasound echo. It provides an output to envelope detector 210.

Envelope detector 210 determines a signal level from a first ultrasound echo that is produced in the region during a first time, which occurs while the contrast agent is present in the region. The output of envelope detector 210 is routed to log amplifier 215, which produces a logarithm of the signal level from the first ultrasound echo. Memory 220 stores the logarithm of the signal level from the first ultrasound echo, and presents it as a first input to subtractor 225.

Subsequently, envelope detector 210 determines a signal level of a second ultrasound echo that is produced in the region during a second time, which occurs after destruction of the contrast agent. The output of envelope detector 210 is routed to log amplifier 215, which produces a logarithm of the signal level from the second ultrasound echo. The logarithm of the second ultrasound echo is presented as a second input to subtractor 225.

Subtractor 225 finds a difference between the logarithm of the signal level from the first ultrasound echo provided by memory 220, and the logarithm of the signal level from the second ultrasound echo provided by log amplifier 215. Thus, the output of subtractor 225 is a logarithm of the ratio of the signal level from the first ultrasound echo and the signal level from the second ultrasound echo. The ratio can be produced either by subtracting the first log signal from the second, or vice versa. A particular designation of a signal level in the ratio as either a numerator or a denominator is not critical to the operation of the invention.

The logarithm of the ratio is routed from the output of subtractor 225 to an input of display 230 for further processing.

FIG. 3 is a block diagram of a system 300, which is another embodiment of a system for detecting a relative level of a contrast agent. System 300 includes a clutter filter 305, an envelope detector 310, a memory 312, a spatial subset selector 315, an averager 320, a divider 325, a log amplifier 330, and a display 335. Clutter filter 305, envelope detector 310 and log amplifier 330 function similarly to clutter filter 105, envelope detector 110, and log amplifier 125, respectively, as discussed above in association with FIG. 1.

In some situations, the relative level of a contrast agent can be more clearly detected by considering an average signal level from ultrasound echoes produced throughout a region of interest. The average signal level can then be used as a reference against which an instantaneous signal level can be compared. More particularly, the instantaneous signal level and the average signal level can be used in a ratio.

Instantaneous Magnitude:Average Magnitude or

Instantaneous Power:Average Power

Clutter filter 305 receives data representing an ultrasound echo. An output of clutter filter 305 is routed to envelope detector 310.

Envelope detector 310 receives the output from clutter filter 305 and detects an instantaneous signal level of the ultrasound echo. The signal level is directly related to the concentration of the contrast agent present in the region of interest. The signal level is also related to other factors such as system gain, filter characteristics, and attenuation of the echo as it propagates through the body. However, taking a ratio of signals tends to minimize the effect of these other factors on the signal level. An output from envelope detector 310 is routed to memory 312.

Memory 312 receives signal level data from envelope detector 310. It stores a frame of data, that is data representing signal levels from ultrasound echoes produced throughout the region of interest. In this embodiment, an output of memory 312 is routed to spatial subset selector 315 and also provided as a first input to divider 325.

Spatial subset selector 315 has access to the frame of data from memory 312. It obtains a plurality of detected signal levels from memory 312 and selects a spatial subset of the region of interest for which an average signal level will subsequently be determined. Spatial subset selector 315 provides, to averager 320, a set of signal levels acquired from the spatial subset.

Averager 320 receives the set of signal levels from spatial subset selector 315 and determines an average signal level of the set. The average signal level is provided as a second input to divider 325.

Divider 325 receives two inputs, one from memory 312 and one from averager 320, and divides one by the other to produce a ratio. More particularly, it receives an average signal level from averager 320 and an instantaneous signal level from memory 312, and produces and output that is a ratio of the average signal level and the instantaneous signal level. The ratio is provided as an input to log amplifier 330.

Log amplifier 330 receives the ratio from divider 325 and produces a logarithm of the ratio of the average signal level and the instantaneous signal level. The output of log amplifier 330 is routed to display 335.

Display 335 receives the logarithm of the ratio and processes it to produce an image. As explained below, display 335 also determines whether blood is flowing into a spatial subset of the region of interest based on the relative level of the contrast agent.

In operation, the components of system 300 collectively execute a method for detecting a relative level of a contrast agent in a region of a body. The method includes the steps of (a) determining an average signal level from a plurality of ultrasound echoes that are produced in a plurality of spatial subsets of the region; (b) determining a signal level from an ultrasound echo that is produced in at least one spatial subset of the region; and (c) determining an arithmetic relationship between the average signal level and the signal level. The arithmetic relationship indicates a relative level of the contrast agent in the at least one spatial subset as compared to the average level in the plurality of spatial subsets.

Memory 312 holds a frame of data. Data corresponding to an instantaneous signal level from an ultrasound echo that is produced in a particular spatial subset of the region is routed from memory 312 to a first input of divider 325. The output of memory 312 is also available to spatial subset selector 315.

Spatial subset selector 315 accesses the frame of data held by memory 312, selects a plurality of spatial subsets and obtains data from the plurality of spatial subsets. Averager 320 determines an average signal level of the plurality of spatial subsets. The average signal level is provided a second input to divider 325.

Divider 325 determines an arithmetic relationship, in this case a ratio, between the average signal level and the instantaneous signal level. The arithmetic relationship indicates a relative level of the contrast agent in the particular spatial subset as compared to the average in the plurality of spatial subsets. A particular designation of a signal level as either a numerator or a denominator is not critical to the operation of the invention.

As the present invention is directed toward a determination of a relative level of the contrast agent, no specific relationship is required between the particular spatial subset and the plurality of spatial subsets. That is, the present invention covers the case where the particular spatial subset is one of the plurality of spatial subsets, and it also covers the case where the particular spatial subset is not one of the plurality of spatial subsets.

The ratio is routed from the output of divider 325 to log amplifier 330, which provides a logarithm of the ratio to display 335 for further processing.

Recall that a flow of blood into a region occurs at a substantially greater rate than a perfusion of blood into the region. Display 335 determines whether blood is flowing into the particular spatial subset based on the relative level of the contrast agent in the particular spatial subset as compared to the average in a predetermined sub-region. Assume that substantially all the contrast agent is purged from the region of interest during a first imaging frame, and then data is collected and stored into memory 312 during a second imaging frame. For example, a plurality of spatial subsets of the region of interest can be selected to define a sub-region into which blood perfuses. Thereafter, the system of FIG. 3 determines the average signal level from the sub-region, and constructs a ratio using the instantaneous signal level from a particular spatial subset in the numerator and using the average signal level in the denominator. If the ratio is substantially greater than 1, than the relative level of contrast agent in the particular spatial subset is greater than the average level in the sub-region, and therefore, blood is likely to be flowing into the particular spatial subset.

In a general case, any arithmetic operation can be performed between the average signal level and the signal level. For example, the arithmetic relationship can be a difference between the average signal level and the signal level.

FIG. 4 is a block diagram of a system 400, which is a variation of system 300 shown in FIG. 3. System 400 includes a clutter filter 405, an envelope detector 410, a log amplifier 415, a memory 417, a spatial subset selector 420, an averager 425, a subtractor 430 and a display 435. Clutter filter 405, envelope detector 410 and display 435 function similarly to clutter filter 305, envelope detector 310 and display 335, respectively, as discussed above in the context of FIG. 3.

System 400 and system 300 differ in the manner in which they determine a logarithm of a ratio of two signals. System 400 determines a difference between a logarithm of an average signal level and a logarithm of an instantaneous signal level. This difference yields a logarithm of a ratio of the average signal level and the instantaneous signal level.

Clutter filter 405 receives data representing an ultrasound echo. It provides an output to envelope detector 410.

Envelope detector 410 receives the output from clutter filter 405 and detects an instantaneous signal level of the ultrasound echo. The output of envelope detector 410 is routed to log amplifier 415, which produces a logarithm of each of the signal levels. The output of logarithmic amplifier 415 is, in turn, routed to memory 417.

Memory 417 holds a frame of data. Data corresponding to a logarithm of an instantaneous signal level from an ultrasound echo that is produced in a particular spatial subset of the region is routed from memory 417 to a first input of subtractor 430. The output of memory 417 is also available to spatial subset selector 420.

Spatial subset selector 420 has access to the frame of data from memory 417. Spatial subset selector 420 selects a spatial subset of the region of interest for which an average logarithmic signal level will subsequently be determined. Spatial subset selector 420 provides to averager 425, a set of logarithmic signal levels acquired from the spatial subset. Averager 425 receives the set of logarithmic signal levels from spatial subset selector 420 and determines the average logarithmic signal level, which is presented as a second input to subtractor 430.

System 400 could be implemented to produce either a logarithm of an average, or an average of a logarithm. Generally, a logarithm compresses a large value and expands a small value. The logarithm of the average is less likely to be dominated by a few small values while, on the other hand, the average of the logarithm is less likely to be dominated by a few large values.

Subtractor 430 finds a difference between the average logarithmic signal level provided by averager 425, and the logarithm of the instantaneous signal level obtained from memory 417. Thus, the output of subtractor 430 is a logarithm of the ratio of the average signal level and the signal level. The ratio can be produced either by subtracting the first signal from the second, or vice versa. A particular designation of a signal level in the ratio as either a numerator or a denominator is not critical to the operation of the invention.

The logarithm of the ratio of the average signal level and the signal level is routed from the output of subtractor 430 to an input of display 435 for further processing.

A particularly useful system results from a combination of the features of a system as shown in FIGS. 1 or 2 and a system as shown is FIGS. 3 or 4. The system shown in FIGS. 1 or 2 determines whether blood perfuses into a region of interest. Therefore, a plurality of spatial subsets of the region of interest can be selected to define a sub-region into which blood perfuses. The system shown in FIGS. 3 or 4 thereafter (a) determines an average signal level from the plurality of spatial subsets, (b) constructs a ratio of an instantaneous signal level from a particular spatial subset and the average signal level, (c) determines a relative level of contrast agent in a particular spatial subset as compared to the average level in the sub-region, and (d) determines whether blood is likely to be flowing into the particular spatial subset.

Figure 5:
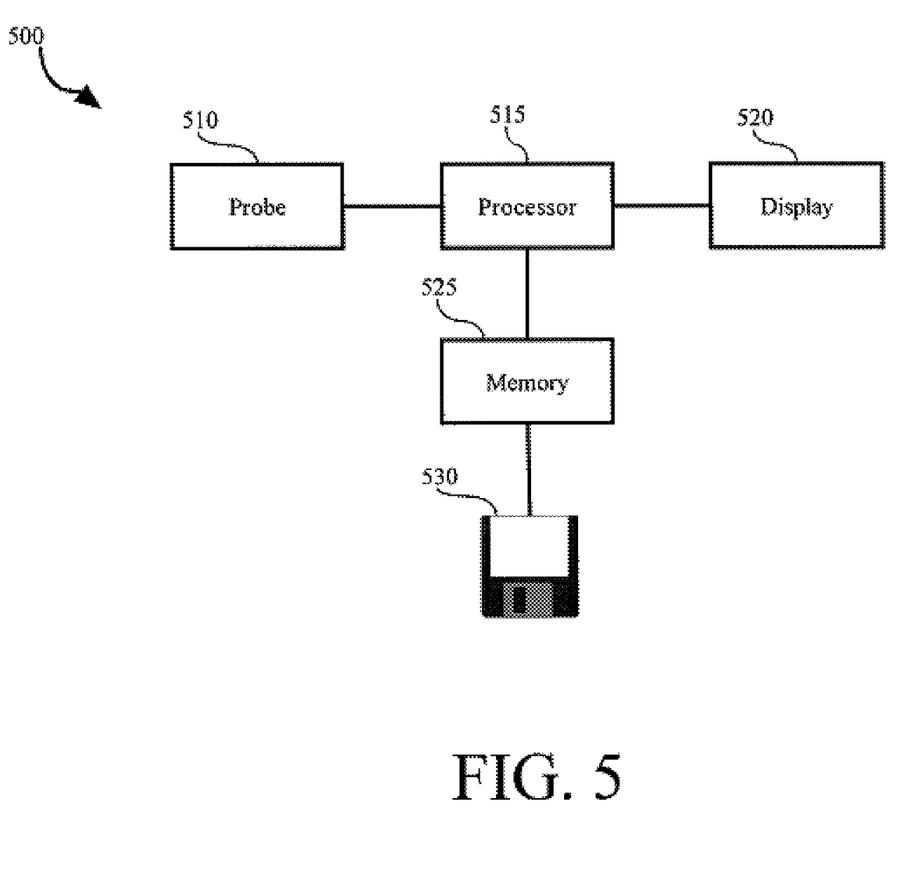
FIG. 5 is a block diagram of an ultrasound system for detecting a relative level of a contrast agent in accordance with the present invention.

FIG. 5 is a block diagram of an ultrasound system 500 for detecting a relative level of a contrast agent in accordance with the present invention. Ultrasound system 500 includes a probe 510, a processor 515, a display 520, and a memory 525.

Probe 510 transmits an ultrasound signal into, and receives an ultrasound echo from, a region of interest in a body. It receives a transmit signal from, and provides a signal representing the ultrasound echo to, processor 515.

Processor 515 executes instructions to perform the methods described above in association with FIGS. 1–4. It can be a special purpose device implemented with discrete components or firmware, or it can be a general-purpose processor. Alternatively, it can be part of an independent unit such as a desktop computer. The output of processor 515 is routed to display 520.

Display 520 can be any conventional display apparatus such as video monitor, or digital display, for providing a visual presentation of an ultrasound image.

Memory 525 contains data and instructions for execution by processor 525. While the procedures required to execute the invention hereof are indicated as already loaded into memory 525, they may be configured on a storage media, such as data memory 530, for subsequent loading into the memory 525.

It should be understood that the foregoing description is only illustrative of the invention. Various alternatives and modifications can be devised by those skilled in the art without departing from the invention. For example, the temporal relationship between an acquisition of ultrasound data and a processing of the data is not critical to the operation of the present invention. That is, the data can be acquired and then either (a) processed in real-time or (b) stored and subsequently processed, off-line. Accordingly, the present invention is intended to embrace all such alternatives, modifications and variances that fall within the scope of the appended claims.

What is claimed is:

1. A method for detecting a relative level of a contrast agent within a selected region of a body wherein the contrast agent is susceptible to destruction by a destructive ultrasound signal, said method comprising the steps of:

(a) determining a first signal level from a first ultrasound echo produced while contrast agent is present in said region;

(b) determining a second signal level of a second ultrasound echo produced after destruction of the contrast agent in said region by the destructive ultrasound signal; and (c) determining a ratio of the first signal level and the second signal level.

2. The method of claim 1, wherein step (a) and step (b) are executed in consecutive ultrasound imaging frames.

3. The method of claim 1, further comprising the step of:
(d) determining whether blood is perfusing into said region based on the ratio.

4. The method of claim 1, wherein step (c) includes the step of determining a difference between a logarithm of the first signal level and a logarithm of the second signal level.

5. The method of claim 1, wherein the first signal is an average signal level from a plurality of ultrasound echoes produced before, or at a time of, destruction of the contrast agent.

6. The method of claim 1, wherein the second signal level is an average signal level from a plurality of ultrasound echoes produced after destruction of said contrast agent.

7. A method for detecting a relative level of a contrast agent in a region of a body, said contrast agent being susceptible to destruction by a destructive ultrasound signal, said method comprising the steps of:
(a) determining an average signal level from a plurality of ultrasound echoes that are produced in a plurality of spatial subsets of said region;
(b) determining a signal level from an ultrasound echo that is produced in at least one spatial subset of said region; and
(c) determining an arithmetic relationship between said average signal level and said signal level, wherein said arithmetic relationship indicates a relative level of said contrast agent in said at least one spatial subset as compared to said plurality of spatial subsets.

8. The method of claim 7, wherein said arithmetic relationship is a difference between said average signal level and said signal level.

9. The method of claim 7, wherein said arithmetic relationship is a ratio of said average signal level and said signal level.

10. The method of claim 9, wherein step (c) includes the step of determining a difference between a logarithm of said average signal level and a logarithm of said signal level.

11. The method of claim 7, wherein said plurality of spatial subsets defines a sub-region into which blood perfuses, and said method further comprises the step of:
(d) determining whether blood is flowing into said at least one spatial subset based on said relative level of said contrast agent, wherein a rate of blood flow is substantially greater than a rate of blood perfusion.

12. A system for detecting a relative level of a contrast agent in a region of a body, said system comprising:
(a) means for determining a first signal level from a first ultrasound echo produced in the region while the contrast agent is present in the region;
(b) means for determining a second signal level of a second ultrasound echo produced in the region after destruction of the contrast agent; and
(c) means to determine a ratio of the first signal level to the second signal level.

13. The system of claim 12, wherein means (a) and means (b) execute their respective actions in consecutive ultrasound imaging frames.

14. The system of claim 12, further comprising:
(d) means for determining whether blood is perfusing into said region based on the ratio.

15. The system of claim 12, wherein means (c) includes means for determining a difference between a logarithm of the first signal level and a logarithm of the second signal level.

16. The system of claim 12, wherein the first signal level is an average signal level from a plurality of ultrasound echoes produced before, or at a time of, destruction of the contrast agent.

17. The system of claim 12, wherein the second signal level is an average signal level from a plurality of ultrasound echoes produced after destruction of the contrast agent.

18. A system for detecting a relative level of a contrast agent in a region of a body, said contrast agent being susceptible to destruction by a destructive ultrasound pulse, said system comprising:
(a) means for determining an average signal level from a plurality of ultrasound echoes that are produced in a plurality of spatial subsets of said region;
(b) means for determining a signal level from an ultrasound echo that is produced in at least one spatial subset of said region; and
(c) means for determining an arithmetic relationship between said average signal level and said signal level, wherein said arithmetic relationship indicates a relative level of said contrast agent in said at least one spatial subset as compared to said plurality of spatial subsets.

19. The system of claim 18, wherein said arithmetic relationship is a difference between said average signal level and said signal level.

20. The system of claim 18, wherein said arithmetic relationship is a ratio of said average signal level and said signal level.

21. The system of claim 20, wherein means (c) includes means for determining a difference between a logarithm of said average signal level and a logarithm of said signal level.

22. The system of claim 18, wherein said plurality of spatial subsets defines a sub-region into which blood perfuses, and said system further comprises:
(d) means for determining whether blood is flowing into said at least one spatial subset based on said relative level of said contrast agent, wherein a rate of blood flow is substantially greater than a rate of blood perfusion.

23. A computer readable storage media storing software for detecting a relative level of a contrast agent in a region of a body, the software causing a processor to perform the following actions:
(a) determining a first signal level from a first ultrasound echo produced from the region while contrast agent is present in said region;
(b) determining a second signal level of a second ultrasound echo produced from the region after destruction of the contrast agent; and
(c) determining a ratio of the first signal level and the second signal level.

24. The storage media of claim 23, wherein action (a) and action (b) execute their respective actions in consecutive ultrasound imaging frames.

25. The storage media of claim 23, further comprising software to perform the following actions:
(d) determining whether blood is perfusing into said region based on the relative level of said contrast agent.

26. The storage media of claim 23, wherein action (c) determines a difference between a logarithm of the first signal level and the second signal level.

27. The storage media of claim 23, wherein the first signal level is an average signal level from a plurality of ultrasound echoes produced before, or at a time of, destruction of the contrast agent.

28. The storage media of claim 23, wherein the second signal level is an average signal level from a plurality of ultrasound echoes produced after destruction of the contrast agent.

29. A computer readable storage media including software for detecting a relative level of a contrast agent in a region of a body, the software causing a processor to perform the following actions:
 (a) determining an average signal level from a plurality of ultrasound echoes that are produced in a plurality of spatial subsets of said region;
 (b) determining a signal level from an ultrasound echo that is produced in at least one spatial subset of said region; and
 (c) determining an arithmetic relationship between said average signal level and said signal level, wherein said arithmetic relationship indicates a relative level of said contrast agent in said at least one spatial subset as compared to said plurality of spatial subsets.

30. The storage media of claim 29, wherein said arithmetic relationship is a difference between said average signal level and said signal level.

31. The storage media of claim 29, wherein said arithmetic relationship is a ratio of said average signal level and said signal level.

32. The storage media of claim 31, wherein action (c) determines a difference between a logarithm of said average signal level and a logarithm of said signal level.

33. The storage media of claim 29, wherein said plurality of spatial subsets defines a sub-region into which blood perfuses, and said storage media further comprises software for performing the following actions:
 (d) determining whether blood is flowing into said at least one spatial subset based on said relative level of said contrast agent, wherein a rate of blood flow is substantially greater than a rate of blood perfusion.

34. A method for determining a relative level of a contrast agent in a region of a body, said contrast agent being susceptible to destruction by a destructive ultrasound signal, said method comprising the steps of:
 measuring signal levels from a plurality of ultrasound echoes that are produced in said region; and
 determining a ratio of a signal level from a first measured ultrasound echo produced while said contrast agent is present in said region, and a signal level from a second measured ultrasound echo produced after a destruction of said contrast agent,
 wherein said ratio indicates a relative level of said contrast agent after said destruction as compared to when said contrast agent was present.

35. A computer readable storage media storing software for detecting a relative level of a contrast agent in a region of a body, the software causing a processor to perform the following actions:
 measuring signal levels from a plurality of ultrasound echoes that are produced in said region;
 determining a ratio of a signal level from a first of said plurality of ultrasound echoes that is produced while said contrast agent is present in said region, and a signal level from a second of said plurality of ultrasound echoes produced after destruction of said contrast agent,
 wherein said ratio indicates a relative level of said contrast agent after said destruction as compared to when said contrast agent was present.

36. A method for determining a relative level of a contrast agent in a region of a body, said contrast agent being susceptible to destruction by a destructive ultrasound signal, said method comprising the steps of:
 measuring signal levels from a plurality of ultrasound echoes that are produced in said region; and
 determining an arithmetic relationship between an average signal level from the plurality of ultrasound echoes that are produced in a plurality of spatial subsets of said region, and a signal level from an ultrasound echo that is produced in at least one spatial subset of said region,
 wherein said arithmetic relationship indicates a relative level of said contrast agent in said at least one spatial subset as compared to said plurality of spatial subsets.

37. A computer readable storage media storing software for detecting a relative level of a contrast agent in a region of a body, the software causing a processor to perform the following actions:
 measuring signals level from a plurality of ultrasound echoes that are produced in said region; and
 determining an arithmetic relationship between an average signal level from the plurality of ultrasound echoes that are produced in a plurality of spatial subsets of said region, and a signal level from an ultrasound echo that is produced in at least one spatial subset of said region,
 wherein said arithmetic relationship indicates a relative level of said contrast agent in said at least one spatial subset as compared to said plurality of spatial subsets.

* * * * *